United States Patent
Karube

(10) Patent No.: US 11,220,658 B2
(45) Date of Patent: Jan. 11, 2022

(54) DETERGENT COMPOSITION, CLEANING METHOD, SOLVENT COMPOSITION, USE THEREOF AS SOLVENT FOR OIL, AND OIL COMPOSITION CONTAINING SAME

(71) Applicant: DAIKIN INDUSTRIES, LTD., Osaka (JP)

(72) Inventor: Daisuke Karube, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/347,899

(22) PCT Filed: Nov. 8, 2017

(86) PCT No.: PCT/JP2017/040206
§ 371 (c)(1),
(2) Date: May 7, 2019

(87) PCT Pub. No.: WO2018/088418
PCT Pub. Date: May 17, 2018

(65) Prior Publication Data
US 2019/0352583 A1    Nov. 21, 2019

(30) Foreign Application Priority Data

Nov. 11, 2016   (JP) .............................. JP2016-220620

(51) Int. Cl.
| C10M 107/00 | (2006.01) |
| C11D 7/50 | (2006.01) |
| C07C 21/18 | (2006.01) |
| C10M 107/38 | (2006.01) |
| C10M 107/50 | (2006.01) |
| C23G 5/028 | (2006.01) |

(52) U.S. Cl.
CPC ............ *C11D 7/5018* (2013.01); *C07C 21/18* (2013.01); *C10M 107/38* (2013.01); *C10M 107/50* (2013.01); *C10M 2213/023* (2013.01); *C10M 2229/025* (2013.01); *C23G 5/02841* (2013.01)

(58) Field of Classification Search
CPC .............. C11D 7/5018; C11D 11/0029; C11D 11/0041; C11D 11/0047; C11D 3/245; C11D 3/43; C07C 21/18; C10M 107/38; C10M 107/50; C10M 2213/023; C10M 2229/025; C10M 131/04; C23G 5/02812; C23G 5/02841; C23G 5/02809
See application file for complete search history.

(56) References Cited

U.S. PATENT DOCUMENTS

| 2,673,173 A | * | 3/1954 | Ruh ....................... C07C 17/25 |
| | | | 514/744 |
| 2,742,428 A | | 4/1956 | Agens et al. |
| 2015/0037505 A1 | | 2/2015 | Tsuzaki et al. |
| 2017/0022603 A1 | | 8/2017 | Deur-Bert et al. |
| 2017/0283648 A1 | | 10/2017 | Mohara et al. |
| 2017/0320798 A1 | | 11/2017 | Shimokawa et al. |
| 2017/0321167 A1 | | 11/2017 | Imura et al. |
| 2019/0127302 A1 | | 5/2019 | Deur-Bert et al. |

FOREIGN PATENT DOCUMENTS

| GB | 700469 | 12/1953 |
| GB | 1087873 | 10/1967 |
| JP | 2001-354985 | 12/2001 |
| JP | 2011-510119 | 3/2011 |
| JP | 2013/224383 | 10/2013 |
| JP | 2013249326 A * | 12/2013 |
| JP | 2016-98334 | 5/2016 |
| WO | 2009/089511 | 7/2009 |
| WO | 2013/161723 | 10/2013 |
| WO | 2014/144558 | 9/2014 |
| WO | 2016/035765 | 3/2016 |
| WO | 2016/059322 | 4/2016 |
| WO | 2016/080283 | 5/2016 |

OTHER PUBLICATIONS

International Search Report dated Dec. 19, 2017 in International (PCT) Application No. PCT/JP2017/040206.
Paleta O. et al., "Addition Reactions of Haloolefins. XII. The Reaction of Trifluorochloroethylene With Monofluorochloromethanes in the Presence of Aluminium Chloride", Collection Symposium Series / Institute of Organic Chemistry and Biochemistry, Academy of Sciences, vol. 36, Jan. 1, 1971, pp. 2257-2266.
Extended European Search Report dated Feb. 28, 2020 in corresponding European Application No. 17869441.0.

* cited by examiner

*Primary Examiner* — Taiwo Oladapo
(74) *Attorney, Agent, or Firm* — Wenderoth, Lind & Ponack, L.L.P.

(57) ABSTRACT

An object of the present invention is to provide a solvent and a detergent that have excellent basic properties as solvents or detergents, such as solubility, and that have a boiling point, flammability, toxicity, GWP, and ODP that are all within preferable ranges. To achieve the above object, the present invention provides a solvent composition or detergent composition comprising a hydrochlorofluoropropene represented by the formula: $CX_3CX=CX_2$, wherein each X is the same or different and is F or Cl, at least one X is F, and at least three X are Cl; the hydrochlorofluoropropene having an atmospheric pressure boiling point of 50° C. or higher.

3 Claims, No Drawings

DETERGENT COMPOSITION, CLEANING METHOD, SOLVENT COMPOSITION, USE THEREOF AS SOLVENT FOR OIL, AND OIL COMPOSITION CONTAINING SAME

RELATED APPLICATION

This application is a national stage entry of PCT/JP2017/040206, filed Nov. 8, 2017, which claims priority from Japanese Patent Application No. 2016-220620, filed Nov. 11, 2016, which are incorporated by reference in their entirety.

TECHNICAL FIELD

The present invention relates to a detergent composition, a cleaning method, a solvent composition, use thereof as a solvent for oil, and an oil composition containing the same.

BACKGROUND ART

Various oils, including lubricating oils, such as silicone oil, fluorine-based oil, mineral-based oil, grease, and wax, are used for various applications. These oils can be singly applied to substrate surfaces or machine part surfaces in need of lubrication; however, in consideration of predetermined necessity or purpose, they are often used after being dissolved in solvents. For example, these oils are used when it is necessary to adjust viscosity etc., or used for the purpose of forming lubricating films of the oils on the surfaces to which the oils are applied.

Moreover, those that have the same composition as these solvents and that are used to dissolve various oils for cleaning are particularly called detergents, cleaning solvents, etc.

Some solvents or detergents are required to be non-flammable. Conventionally used non-flammable solvents are fluorine-based solvents with low toxicity, represented by trade names "Asahiklin AK-225," "Zeorola H," "Novec," etc.

However, it is indicated that these conventional fluorine-based solvents or detergents, which are advantageous in non-flammability and low toxicity, have problems in terms of environmental destruction, such as possibility of ozone layer depletion and possibility of contribution to global warming. In consideration of these circumstances, products, such as various hydrofluoroolefins and 1,2-dichloroethylene, have been developed as environmentally friendly solvents. Examples include chlorofluoroolefin (boiling point 46° C.) (PTL 1), hydrochlorofluoroolefin (boiling point: 53° C.) (PTL 2), 1,2-dichloroethylene (boiling point: 48° C.), a mixture of 1,2-dichloroethylene and hydrofluoroolefin mentioned above, and cyclic hydrofluorocarbon (boiling point: 83° C.) (PTL 3), and the like.

In contrast, however, these environmentally friendly solvents have various problems such that they have low solubility; the solvents themselves are flammable; when they are mixed with second non-flammable solvents to reduce the flammability of the solvents themselves, it is necessary to adjust the composition ratio so that the mixed solvents are azeotropic; their boiling point is not suitable; and reduction in the global warming potential is not sufficient.

CITATION LIST

Patent Literature

PTL 1: JP2013-224383A
PTL 2: JP2016-98334A
PTL 3: JP2001-354985A

SUMMARY OF INVENTION

Technical Problem

An object of the present invention is to provide a solvent and a detergent that have excellent basic properties as solvents or detergents, such as solubility, and that have a boiling point, flammability, toxicity, GWP, and ODP that are all within preferable ranges.

Solution to Problem

The present inventor found that the above object can be achieved by a solvent composition or detergent composition comprising a hydrochlorofluoropropene represented by the formula: $CX_3CX=CX_2$, wherein each X is the same or different and is F or Cl, at least one X is F, and at least three X are Cl; the hydrochlorofluoropropene having an atmospheric pressure boiling point of 50° C. or more.

The present invention has been completed upon further trial and error based on the above finding. The present invention includes the following aspects.

Item 1. A solvent composition or detergent composition comprising a hydrochlorofluoropropene represented by the formula: $CX_3CX=CX_2$, wherein each X is the same or different and is F or Cl, at least one X is F, and at least three X are Cl;

the hydrochlorofluoropropene having an atmospheric pressure boiling point of 50° C. or more.

Item 2. The solvent composition or detergent composition according to Item 1, wherein the hydrochlorofluoropropene is 1,1,2-trichloro-3,3,3-trifluoropropene (CFO-1213xa) and/or 1,1,3-trichloro-2,3,3-trifluoropropene (CFO-1213ya).

Item 3. The solvent composition or detergent composition according to Item 1 or 2, further comprising one or more other solvents.

Item 4. The solvent composition or detergent composition according to Item 3, wherein the one or more other solvents are 1,2-dichloroethylene and/or isopropanol.

Item 5. The solvent composition or detergent composition according to any one of Items 1 to 4, for use as a solvent or detergent for oil.

Item 6. The solvent composition according to item 5, wherein the oil is a lubricating oil.

Item 7. The solvent composition according to Item 6, wherein the lubricating oil is at least one lubricating oil selected from the group consisting of silicone-based oil, fluorine-based oil, mineral oil-based oil, grease, and wax.

Item 8. An oil composition comprising oil and the solvent composition according to any one of Items 1 to 4.

Item 9. The oil composition according to Item 8, wherein the oil is a lubricating oil.

Item 10. The oil composition according to Item 9, wherein the lubricating oil is at least one lubricating oil selected from the group consisting of silicone-based oil, fluorine-based oil, mineral oil-based oil, grease, and wax.

Item 11. A cleaning method comprising the step of applying the detergent composition according to any one of Items 1 to 4 to a surface to be treated.

Advantageous Effects of Invention

The present invention can provide a solvent or a detergent that have excellent basic properties as solvents or detergents, such as solubility, and that have a boiling point, flammability, toxicity, GWP, and ODP that are all within preferable ranges.

DESCRIPTION OF EMBODIMENTS

1. Solvent Composition or Detergent Composition
1.1. Hydrochlorofluoropropene

The present invention uses a hydrochlorofluoropropene represented by the formula: $CX_3CX{=}CX_2$, wherein each X is the same or different and is F or Cl, at least one X is F, and at least three X are Cl; the hydrochlorofluoropropene having an atmospheric pressure boiling point of 50° C. or more.

The examination by the present inventor revealed that hydrochlorofluoropropenes represented by the above formula are suitable as solvent components or detergent components that have excellent basic properties as solvents or detergents, such as solubility, and that have flammability, toxicity, GWP, and ODP that are all are within preferable ranges. These hydrochlorofluoropropenes often have an atmospheric pressure boiling point of 50° C. or more, and are also preferably used as solvent components or detergent components in terms of boiling point. Examples of hydrochlorofluoropropenes that have an atmospheric pressure boiling point of 50° C. or more include 1,1,2-trichloro-3,3,3-trifluoropropene (CFO-1213xa), 1,1,3-trichloro-2,3,3-trifluoropropene (CFO-1213ya), and the like. The atmospheric pressure boiling point of CFO-1213xa is 88° C., and the atmospheric pressure boiling point of CFO-1213ya is 87° C.

1.2. Other Solvents

The solvent composition or detergent composition of the present invention may further comprise one or more other solvents.

The one or more other solvents are mixed for the purpose of, for example, further improving the solubility of the object, The one or more other solvents are not limited, and can be widely used. Examples include 1,2-dichloroethylene, isopropanol, and the like. The solvent composition or detergent composition of the present invention comprises one or more other solvents in an amount of 1 to 90 wt. %, and preferably 5 to 50 wt. %, based on the total amount of the solvents.

1.3. Other Components

The solvent composition or detergent composition of the present invention may further comprise one or more other components.

Examples of the one or more other components common in the solvent composition and detergent composition of the present invention include antioxidants, stabilizers, preservatives, surfactants, and the like. The solvent composition or detergent composition of the present invention may comprise at least one member selected from the above group as the one or more other components, As a component different from the above components, the solvent composition of the present invention may further comprise at least one member selected from the group consisting of a lubricant for improving lubrication performance, and a dispersant.

As a component different from the above components, the detergent composition of the present invention may further comprise a surfactant etc, The solvent composition or detergent composition of the present invention comprises the above hydrochlorofluoropropene in a total amount of 1 to 100 wt. % based on the entire composition. In terms of the performance of dissolving an object and/or reducing the flammability as the entire composition, the hydrochlorofluoropropene is preferably contained in a total amount of 5 to 100 wt. %, and more preferably 50 to 100 wt. %, based on the entire composition.

1.4. Application

The solvent composition or detergent composition of the present invention is not limited, and can be used for a wide range of applications. For example, the solvent composition or detergent composition of the present invention is used as a solvent or detergent for oil.

The oil is not limited, and the solvent composition or detergent composition of the present invention can be used for a wide range of oils. In particular, one use of the solvent composition, for example, is being effectively used as a solvent for lubricating oils.

The lubricating oils are not limited, and the solvent composition can be used for a wide range of lubricating oils. Examples of lubricating oils include silicone-based oil, fluorine-based oil, mineral oil-based oil, grease, wax, and the like. The solvent composition of the present invention may be used for one of these lubricating oils, or may be used for a combination of two or more lubricating oils.

The specific use of the detergent composition is not limited to oil, and a wide range of contaminants can be used as cleaning objects. Examples include photoresist, solder flux, resin processing waste, mold releasing agent, working oil, dust, ink, dye, and the like. Moreover, the detergent composition can also be widely used in cleaning methods targeted for oil. Examples include cleaning of precision machinery components, automobile components, electronic components, such as ICs, printed circuit boards, liquid crystal display devices, and magnetic recording devices, as well as optical components, such as optical lenses and optical sensors; cleaning in the production process, assembling process, finishing process, etc., of resin processed products, metal molded products, etc.; and cleaning of processing molds etc.

2. Oil Composition

The oil composition of the present invention comprises oil and the above solvent composition.

For the oil, the same explanation as for the solvent composition is applied.

The oil composition of the present invention is not limited, and may generally comprise 1 to 50 wt. % of oil based on the entire composition, although it depends on the type of oil, application, etc.

The oil composition of the present invention is not limited, and can be used for a wide range of applications. For example, the oil composition of the present invention is used for lubrication of substrate surfaces or machine part surfaces. In that case, the oil composition can be applied to substrate surfaces or machine part surfaces in need of lubrication in such a manner that the oil composition directly exhibits lubricating action. Alternatively, a lubricating film comprising the oil composition can be formed on these surfaces.

3. Cleaning Method

The cleaning method of the present invention comprises the step of applying the detergent composition of the present invention to a surface to be treated.

The surface to be treated is not limited, and can be widely selected. Articles that have a surface to be treated are not limited. The entirety of an article may be used as a surface to be treated, or at least one portion can be used as a surface to be treated.

Specific examples of the cleaning method include cleaning of solder flux, dust, photoresist, etc., in the production process of electronic components, such as ICs, printed circuit boards, liquid crystal display devices, and magnetic recording devices, as well as in the production process of optical components, such as optical lenses and optical sensors; and cleaning of mold releasing agents, working oil, etc., in the production process of precision machinery components, automobile components, resin processed products, metal molded products, etc.

EXAMPLES

The present invention is described in detail below with reference to Examples and Comparative Examples; however, the present invention is not limited thereto.

Example 1

When 50 g of silicone oil having a viscosity at 25° C. of about 10,000 cP and 100 g of CFO-1213ya are mixed, the two components are compatible with each other, and a homogeneous solution can be obtained. The GWP of CFO-1213ya is 10 or less. Further, when measurement using a Setaflash closed-cup tester is carried out, CFO-1213ya has no flash point and is non-flammable.

Example 2

When 100 g of silicone oil having a viscosity at 25° C. of about 10,000 cP, 85 g of CFO-1213ya, and 15 g of 1,2-dichloroethylene are mixed, the three components are compatible with each other, and a homogeneous solution can be obtained.

Example 3

When 3 g of fluorine polymer oil having a viscosity at 25° C. of about 15,000 cP and 100 g of CFO-1213ya are mixed, the two components are compatible with each other, and a homogeneous solution can be obtained.

Comparative Example 1

When 3 g of fluorine-based oil having a viscosity at 25° C. of about 15,000 cP and 100 g of 1,2-dichloroethylene are mixed, the two components are not compatible with each other, and are separated.

The invention claimed is:

1. A cleaning method comprising applying a composition to a surface to be treated, wherein the composition comprises 1,1,3-trichloro-2,3,3-trifluoropropene (CFO-1213ya) as a solvent, the surface to be treated comprises silicone oil and/or fluorine oil, and the solvent dissolves the silicone oil and/or fluorine oil.

2. The cleaning method according to claim 1, wherein the composition further comprises one or more other solvents.

3. The cleaning method according to claim 2, wherein the one or more other solvents are 1,2-dichloroethylene and/or isopropanol.

* * * * *